(12) United States Patent
Christensson

(10) Patent No.: US 6,716,070 B2
(45) Date of Patent: Apr. 6, 2004

(54) BIOMEDICAL PATIENT ELECTRODE CLASP WITH AUTOMATIC STUD LOCK

(75) Inventor: Eddy K. G. Christensson, Edina, MN (US)

(73) Assignee: Cardio Connector Corp., Edina, MN (US)

( * ) Notice: Subject to any disclaimer, the term of this patent is extended or adjusted under 35 U.S.C. 154(b) by 0 days.

(21) Appl. No.: 10/266,117

(22) Filed: Oct. 7, 2002

(65) Prior Publication Data

US 2003/0068918 A1 Apr. 10, 2003

Related U.S. Application Data

(60) Provisional application No. 60/327,483, filed on Oct. 6, 2001.

(51) Int. Cl.[7] .................................................. H01R 4/48
(52) U.S. Cl. ........................ 439/859; 439/729; 439/909
(58) Field of Search ................................ 439/859, 729, 439/909, 261

(56) References Cited

U.S. PATENT DOCUMENTS 3,404,367 A * 10/1968 Herschen .................... 439/634
3,711,819 A * 1/1973 Matthews .................... 439/682
3,842,394 A * 10/1974 Bolduc ........................ 439/261
4,555,155 A * 11/1985 Drake ......................... 439/592
5,624,281 A * 4/1997 Christensson ............... 439/729
5,944,562 A * 8/1999 Christensson ............... 439/729

* cited by examiner

Primary Examiner—Hae Moon Hyeon
(74) Attorney, Agent, or Firm—James V. Harmon

(57) ABSTRACT

In order to lock an electrical clasp to a biomedical electrode stud which projects upwardly from the center of the biomedical electrode, the clasp is provided with an opening in its lower surface for the stud of the biomedical electrode and a downwardly extending tab that has a concave surface facing the stud of the electrode. The concave surface of the tab can be either trough-shaped or spoon-shaped. During operation the tab is moved downwardly from a disengaged position into contact with the sidewall of the stud. In addition, there is a laterally extending tab-retaining edge or rim within the opening and the edge is aligned vertically below the tab so that during use it acts as a backing for the free end of the tab which engages the stud somewhat below the widest part of the head of the stud thereby locking the stud in place within the clasp. Optionally, the clasp includes a plug receptacle that has a converging passage for the plug with electrically conductive resilient walls.

7 Claims, 5 Drawing Sheets

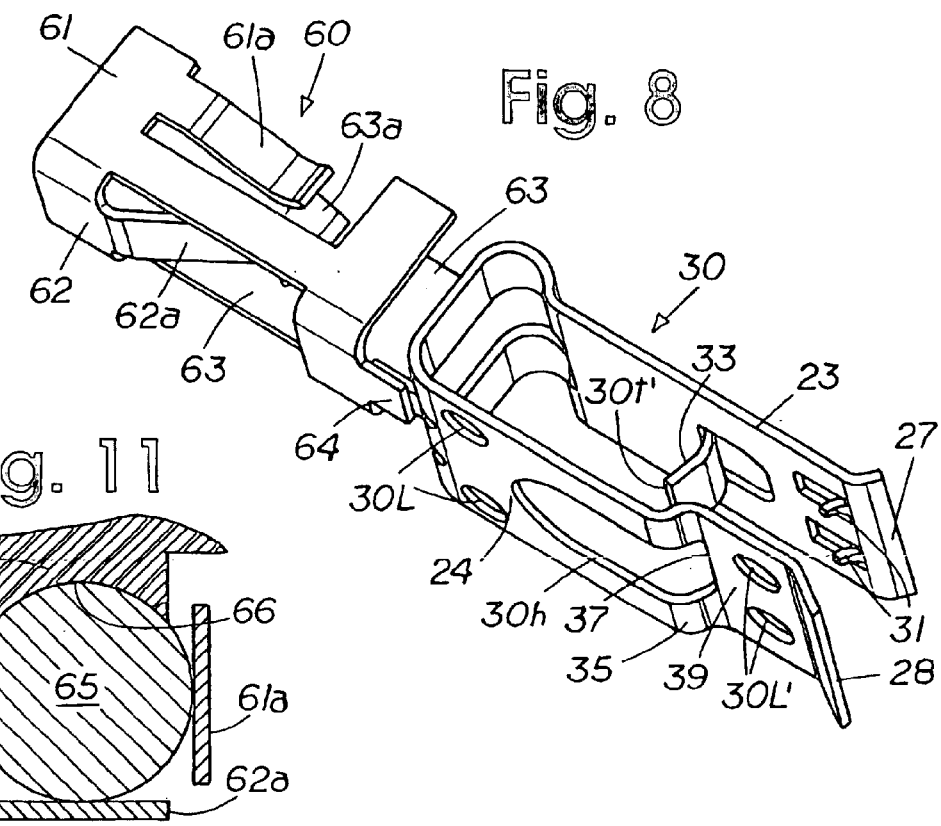
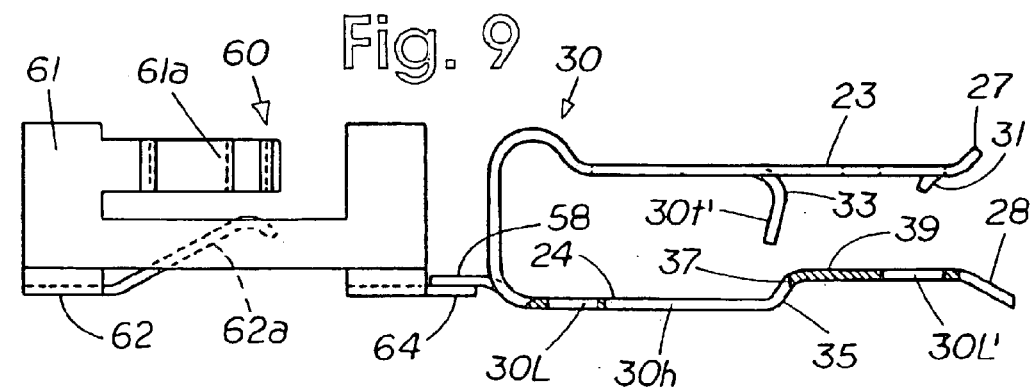
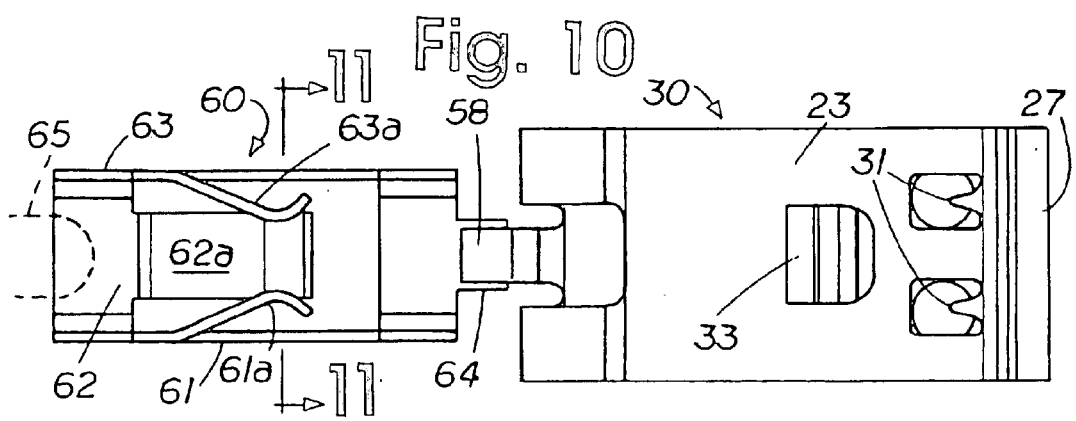

ated similarly except for the automatic locking spring

BIOMEDICAL PATIENT ELECTRODE CLASP WITH AUTOMATIC STUD LOCK

This application claims the benefit of Provisional Application No. 60/327,483, filed Oct. 6, 2001.

FIELD OF THE INVENTION

This invention relates to an electrical clasp that locks automatically to the stud of a biomedical electrode.

BACKGROUND OF THE INVENTION

One general objective of the present invention is to provide a biomedical electrical clasp that can be connected to a laterally extending tab of a tab-style electrode or, if desired can be also connected to the stud of an electrode that has a metallic stud extending upwardly at its center. A clasp that can do both jobs, for convenience, can be thought of as a universal clasp since it can be used for either purpose. The present invention can also however, be employed with clasps that are used only for clasping the stud of a stud-style electrode.

While prior U.S. Pat. No. 5,944,562 describes a clasp that has many advantages, and will resist separation from a stud when lifted straight up, it will sometimes become disengaged from the stud when the cord 78, 79 is pulled horizontally. In a series of tests it was discovered that the stud could become disengaged even when the operating lever was placed in a closed, i.e., operating position.

Thus, prior electrode clasps had certain disadvantages and in particular could not provide the secure electrical contact and mechanical stability that is necessary when connected to the snap-style contact stud. It will be understood that a clasp that has a loose connection or comes off the stud can result in much frustration for the EKG Operator since such disconnections can ruin the recording and prevent the recording machine from properly performing the tests. This occurrence would require repeat tests and manual re-securing of prior art connections to the patient electrodes. During use, the clasp of the present invention is connected to a male electrical pin or plug of either 3 mm or 4 mm in diameter. Most prior clasps are however unable to accept male electrical contact plugs of different sizes.

In view of these shortcomings, one specific object of the invention is to provide a clasp of the type described which has an operating lever that when thrown into the operating or closed position, will automatically lock the clasp to the stud so that the clasp cannot be removed either by lifting it, pulling it horizontally or by wiggling the clasp.

Yet another object is to accommodate male electrical plugs of different sizes, e.g., either 3 or 4 mm in diameter. These and other more detailed and specific objects of the present invention will be better understood by reference to the following figures and detailed description which illustrate by way of example but a few of the various forms of the invention within the scope of the appended claims.

THE FIGURES

FIG. 8 is a perspective view of another form of locking spring.

FIG. 9 is a side view of FIG. 8

FIG. 10 is a top partial view of FIG. 9 and

FIG. 11 is a partial cross-sectional view taken on line 11—11 of FIG. 10

SUMMARY OF THE INVENTION

The present invention overcomes certain of the problems associated with the prior art and the disadvantages thereof by providing an automatic lock which securely engages a biomedical electrode stud and holds it in a manner that prevents it from being released until the operating lever is moved manually to an open or disengaged position.

In order to lock an electrical clasp to the biomedical electrode stud which projects upwardly from the center of the patient electrode, the clasp is provided with an opening in its lower surface for the stud of the patient electrode. Within the clasp is a movable element having a downwardly extending tab that has a concave surface facing the stud of the electrode. The concave surface of the tab can be either trough-shaped or spoon-shaped. During operation the tab is moved downwardly from a disengaged position into contact with the sidewall of the stud. In addition, the opening has a laterally extending tab-retaining edge or rim and the edge or rim is aligned vertically below the tab so that during use the edge acts as a backing for the free end of the tab which engages the stud somewhat below the widest part of the head of the stud thereby locking the stud in place within the clasp. An operating lever retains the tab in its locking position. A receptacle having a converging passage accommodates contact plugs of different sizes.

DETAILED DESCRIPTION

Figure 1:
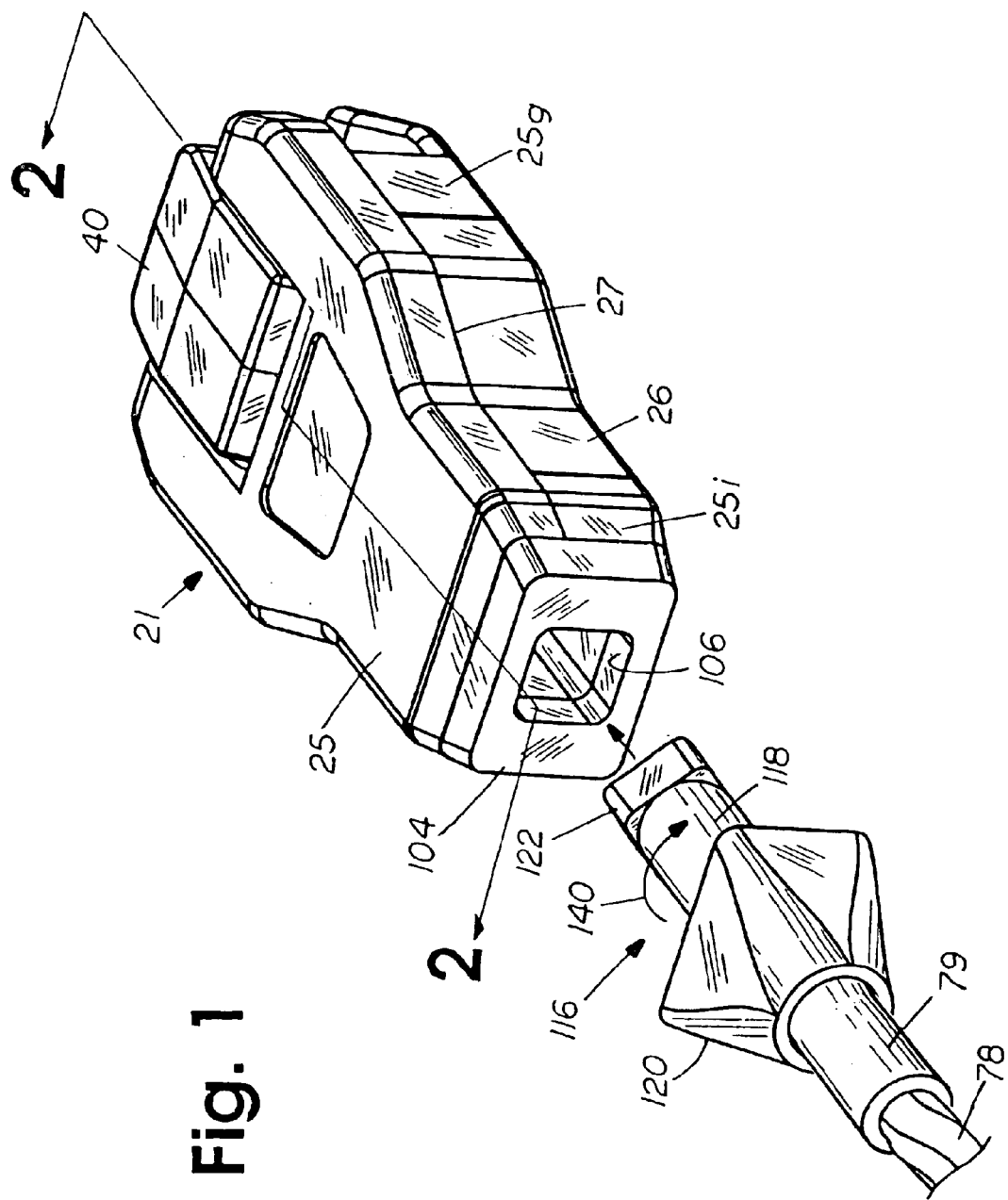
FIG. 1 is a top perspective view of the invention.

Refer now to FIG. 1 which shows a top perspective view of a clasp 21 in accordance with the present invention which is similar to the clasp described in U.S. Pat. No. 5,944,562 except for the locking spring 30 and receptacle 60. U.S. Pat. No. 5,944,562 is incorporated herein by reference. The jaws 27, 28 operate the same as in prior U.S. Pat. No. 5,944,562. The spring 30 and locking tab 30t (FIGS. 4–6) are, however, constructed differently and operate in a different manner as will now be described.

Figure 2:
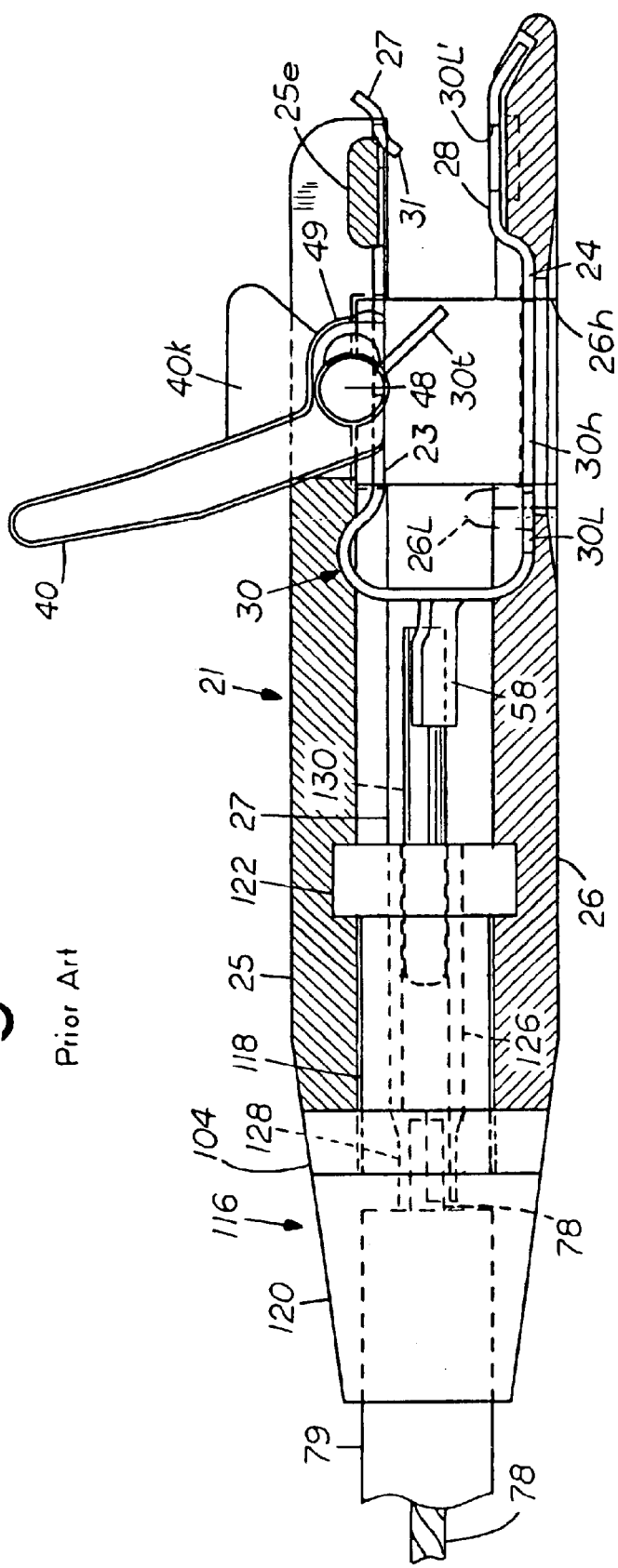
FIG. 2 is a horizontal, cross-sectional view of the clasp taken on-line 2—2 of FIG. 1.
Figure 3:
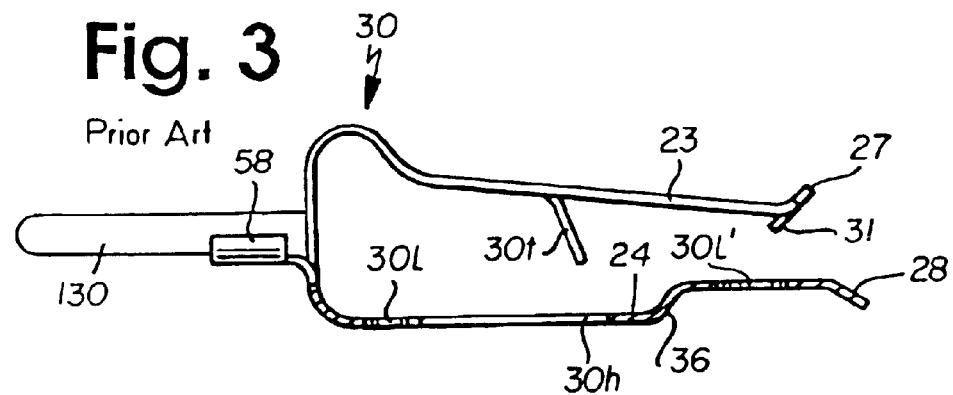
FIG. 3 is a side elevational view of a stud-engaging spring according to the prior art.
Figure 4:
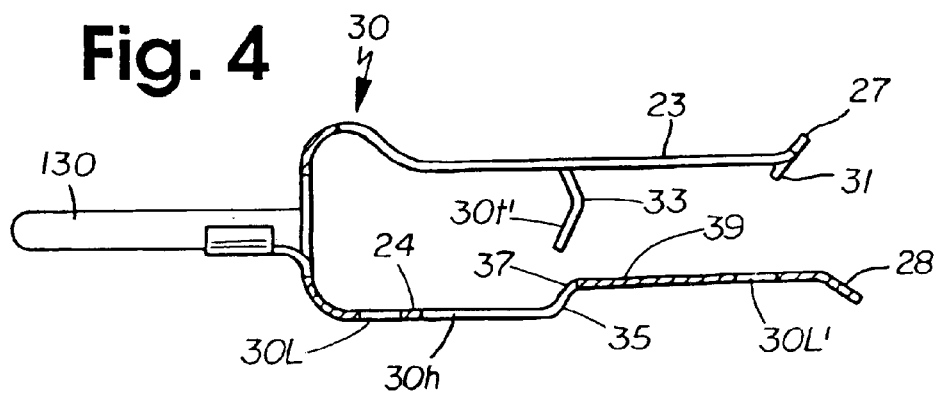
FIG. 4 is a side elevational view of the stud-engaging spring having the automatic stud locking feature in accordance with the present invention.
Figure 5:
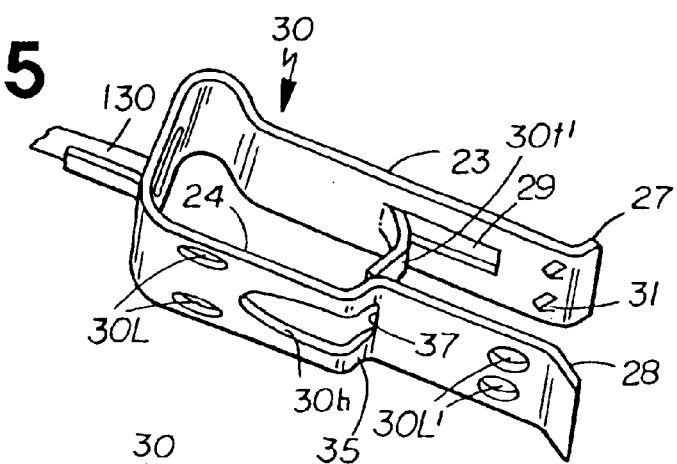
FIG. 5 is a bottom perspective view of the spring of FIG. 4.
Figure 6:
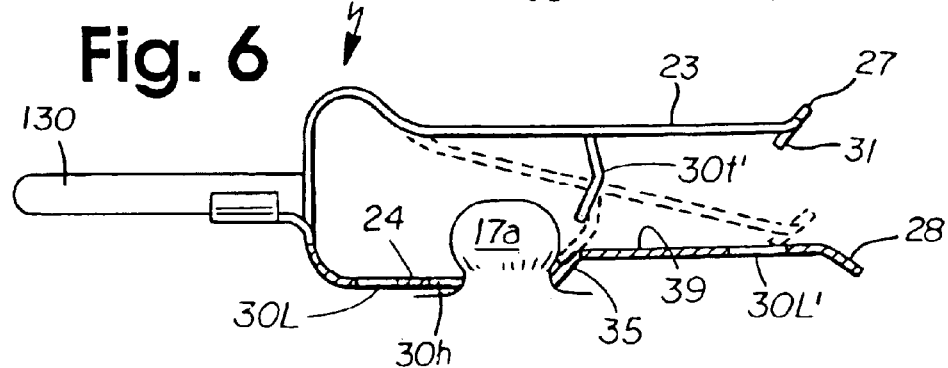
FIG. 6 is a side elevational view of the spring showing the inner spring in the stud-locking position in dotted lines.

FIG. 2 shows the vertical cross-sectional view of the clasp in accordance with the prior art U.S. Pat. No. 5,944,562 with the same numerals designating corresponding parts in the present invention. As already noted, the present invention is constructed similarly except for the automatic locking spring 30 which is shown in FIGS. 4–6 and the receptacle 60 (FIGS. 8–10). For purposes of comparison, the prior art spring of U.S. Pat. No. 5,944,562 is shown in FIG. 3.

Figure 7:
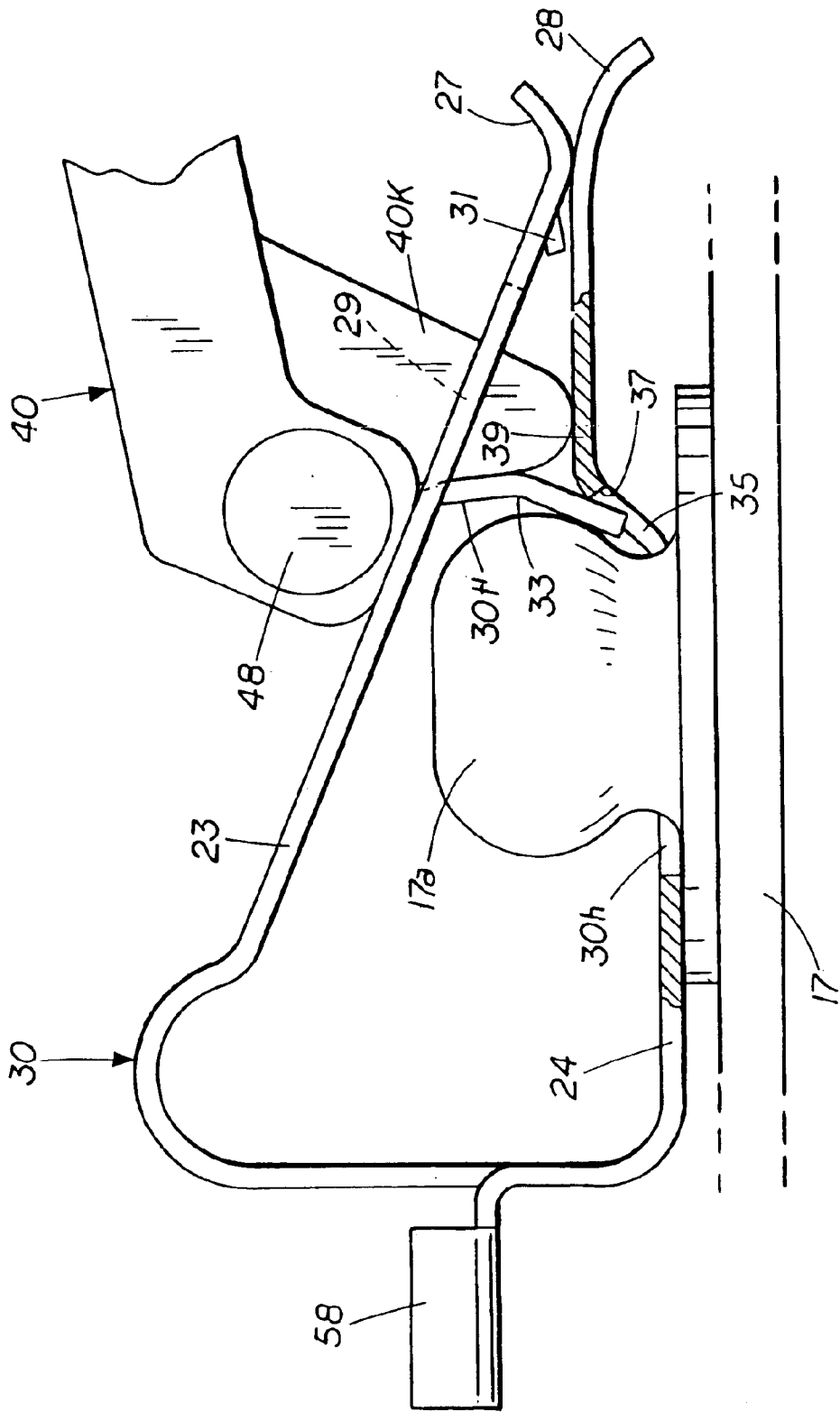
FIG. 7 is a side elevational view of the new automatic locking spring on a larger scale as it appears in the locked position for 562 wherein the same numerals refer to corresponding parts in the prior patent which is incorporated herein by reference.

As in U.S. Pat. No. 5,944,562, the upper portion 25 of the clasp is pressed downwardly during assembly onto the lower portion 26 of the clasp with the spring 30 placed as shown in FIG. 2 so that the spring 30 becomes enclosed between them. The lower portion 26 of the clasp has a hole 26h to receive a metallic stud 17a (FIGS. 6 and 7) of a patient electrode 17 that is used, for example, for heart monitoring or stimulation. The operating lever 40 is pivotally mounted as described in the U.S. Pat. No. 5,944,562 above spring 30. When the operating lever 40 is thrown forwardly so as to pivot in a clockwise direction about the pivot 48, the cam portion engaging the upper surface of the spring 30 will press the upper jaw element 27 of the spring 30 downwardly to a closed position shown by dotted lines in FIG. 6 and by solid lines in FIG. 7. If the biomedical patient electrode (not shown) has a laterally extending tab as described in U.S. Pat. No. 5,944,562, it is engaged between the jaw portions 27 and 28 of the spring 30 and is securely held between them by the teeth or barbs 31 as described in the prior patent. The keel portion 40k of the lever 40 passes through an opening 29 in the top of the spring 30 and finally comes to rest in a position abutting the front surface of the tab 30t' (FIG. 7).

The new leaf spring 30 in accordance with the present invention which is shown in FIGS. 4–7, is constructed to provide an automatic locking feature. First it will be seen that the tab 30t' of FIG. 4 has been made trough-shaped or spoon-shaped by providing a central horizontal bend 33 with a concave surface directed rearwardly, i.e., away from the (distal) jaw end of the clasp 21. In addition, the spring 30 is provided with an upward bend 35 that is aligned vertically below the tab 30t'. The spring 30 in the present invention has an opening 30h with a straight laterally extending tab-retaining edge or rim 37 that cooperates with tab 30t' to hold the stud 17a during operation in a locked position.

It will be noted that as the tab 30t' is pressed downwardly by the operating lever 40, two things are accomplished. First, the tab 30t' curves around the side-wall of the stud 17a engaging its forward surface while at the same time sliding downwardly so as to rest against the rearwardly facing tab-retaining edge 37 of the opening 30h. Thus when the tab 30t' is in the operating or engaged position (FIG. 7), its front surface rests against the rearwardly facing tab-retaining edge 37 of the opening 30h which gives it support and prevents it from bending forwardly thereby securely holding the stud in a locked position so that even if a person attempts to move the clasp 21 in various directions, or wiggles it, the tab 30t' automatically locks it in place and reliably prevents the clasp 21 from becoming separated from the stud 17a of the electrode 17. Thus, during operation, when the clasp is in the locked position, the forward edge 37 of the opening 30h acts as a secure backing or stop for the tab 30t' which because it is aligned over the forward edge 37 of the opening 30h is able to enter the opening when it is pressed downwardly to the locking position by the lever 40.

Refer now to FIGS. 8–11 which illustrate an optional preferred form of plug receptacle for receiving and making electrical contact with a male electrical pin or plug that extends from the free end of a lead wire to which the clasp is connected. The plug receptacle is indicted generally by the numeral 60. As shown in the figures, the plug receptacle 60 comprises a receptacle body formed from sheet metal including three walls comprising right and left sidewalls 61 and 63 and a bottom wall 62 giving the plug receptacle 60 a generally U-shaped configuration as seen in cross-section that is open at the top. The bottom wall 62 has a forwardly extending tongue 64 which is silver-soldered, spot-welded or otherwise secured to the lug 58 of the spring 30 in place of pin 130.

Each of the walls 60, 61, 62 of the receptacle 60 has portions cut away to provide three forwardly projecting centrally inclined outwardly yieldable leaf spring elements designated 61a, 62a, and 63a respectively which together define a passage for a male electrical pin or plug 65. The passage for the plug 65 converges centrally proceeding toward the distal or right end of the clasp as seen in FIGS. 8–10. It will be noted from FIG. 10 that the axis of each of the leaf spring elements 61a–63a points generally in the same direction that the plug 65 is inserted into the receptacle 60, i.e., the free end of each of the spring elements is located distally of its fixed end. Since the resilient leaf spring elements 61a, 62a, and 63a have free ends that are yieldably biased centrally, the passage between them is able to accommodate male electrical plugs 65 of different sizes including those that are either 3 mm or 4 mm in diameter. The upper portion of the clasp 25 has a trough-shaped, i.e., concave bearing surface 66 (FIG. 11) against which the plug 65 slides to help guide the plug 65 as it is inserted into the clasp 21.

During use, when the metallic male plug element 65 which extends from the free end of a lead wire (not shown) is inserted into the clasp 21, its end will slide inwardly (toward the right in the figures) between the free ends of the centrally inclined leaf spring elements 61a–63a to thereby establish electrical contact between the lead wire plug 65 and the locking spring 30. The inclined converging walls of the passage defined by the spring elements 61a–63a and the ability of their free ends to spread apart along two different axes, i.e., side-to-side as well as vertically, makes it possible to establish good electrical contact with male plug elements 65 of different sizes.

Many variations of the present invention within the scope of the appended claims will be apparent to those skilled in the art once the principles described herein are understood.

What is claimed is:

1. A self-locking biomedical electrical clasp for establishing electrical connection to a snap-style patient electrode which has a stud projecting upwardly from a top surface thereof, said clasp comprising, a clasp body including a hole to receive an enlarged head of a stud on a biomedical patient electrode that is used to make electrical contact with the skin of a patient, an operating lever moveably mounted on the clasp body, an electrical conductor having a moveable jaw element connected to the clasp body for establishing electrical contact with the stud when the stud is inserted into the clasp, a locking tab supported on the jaw element above the hole and operatively associated with the operating lever for being moved into contact with the stud when the operating lever is placed in an operating position, a central horizontal bend in the tab that is space apart from the jaw element said tab has a concave surface defined by the bend facing the stud so as to contact an outwardly curved forward surface sidewall of the enlarged head of the stud when moved to an operating position by the operating lever with said bend in the tab thereby curving the tab around the sidewall of the head so as to engage said forward surface thereof and the tab is constructed and positioned with respect to the hole in the clasp to lock the stud within the hole when the lever is moved to a position that lowers the tab into engagement with the stud.

2. The clasp of claim 1 wherein the electrical conductor has an opening therein aligned above the hole in the clasp for admitting the stud when the stud is inserted into the clasp.

3. The clasp of claim 2 wherein the opening in the electrical conductor has a laterally extending tab-retaining edge therein that is aligned below the tab for engaging the tab such that said edge is a stop for the tab to provide horizontal support for the tab by holding a free edge of the tab against the stud while allowing the tab to move vertically to thereby secure the tab in the locking position.

4. A self-locking biomedical electrical clasp for establishing electrical connection to a snap-style patient electrode having a stud projecting upwardly from the top surface thereof, said clasp comprising, An electrode clasp, said clasp being adapted to receive a stud of a biomedical patient electrode that is used to make electrical contact with the skin of a patient, said clasp having an operating lever mounted for movement thereon, an electrical conductor connected to the clasp for establishing electrical contact with the stud when the stud is inserted into the clasp, said electrical conductor comprising a leaf spring with an opening therein for admitting a stud of a patient electrode when the stud is inserted into the clasp, a locking tab depending downwardly from an upper portion of the leaf spring and operatively associated with the operating lever so as to move into contact with the stud when the operating lever is placed in an operating position, said tab being shaped to contact a sidewall of the stud when moved to an operating position by the operating lever and the tab is constructed and positioned with respect to the opening to lock the stud within the opening such that an edge of the opening serving as a stop for the tab that provides horizontal support for the tab while allowing the tab to move vertically, when the lever is moved to an operating position in which the tab is lowered into engagement with the stud.

5. The clasp of claim 4 wherein the edge of the opening in the electrical conductor is aligned below the tab and faces a rear end of the clasp for holding a free edge of the tab against the stud to thereby secure the tab in a stud locking position by preventing forward movement thereof.

6. The clasp of claim 4 wherein the opening in the leaf spring has a straight laterally extending tab-supporting edge portion that is aligned vertically below the tab for engaging an outer surface of the tab opposite a concave surface thereof when the tab is placed in an operating position for holding the tab in engagement with a sidewall of a stud to thereby secure the tab in the stud locking position.

7. A biomedical electrical clasp for establishing electrical connection to a snap-style patient electrode, said clasp comprising, a clasp body including an electrical conductor therein for establishing electrical contact with a biomedical patient electrode that is inserted into the clasp, said electrical conductor including a plug receptacle for receiving an electrically conductively male plug element of a lead wire, said plug receptacle including a plurality of centrally inclined outwardly yieldable leaf spring elements to define a passage for the male plug element, said passage having walls that converge centrally proceeding toward a distal end of the clasp to thereby enable the receptacle to accommodate male plug elements of differing diameters, the plug receptacle includes at least a pair of laterally disposed opposing leaf spring elements confronting one another on each side of the receptacle and a lower leaf spring element that is positioned intermediate the opposing leaf spring elements, the lower leaf spring has a free end that is forced downwardly when the plug is inserted into the clasp and said clasp has a non-resilient bearing surface for contacting a surface of the male plug element opposite said lower leaf spring against which the male plug element slides to guide the plug.

* * * * *